United States Patent [19]

Sinko

[11] 4,453,927
[45] Jun. 12, 1984

[54] METHOD AND APPARATUS FOR MICROFILTRATION OF BLOOD

[75] Inventor: George E. Sinko, San Antonio, Tex.

[73] Assignee: Gesco International, San Antonio, Tex.

[21] Appl. No.: 165,793

[22] Filed: Nov. 12, 1980

Related U.S. Application Data

[63] Continuation-in-part of Ser. No. 10,064, Feb. 7, 1979, abandoned, and a continuation-in-part of Ser. No. 362,427, Mar. 23, 1982, abandoned.

[51] Int. Cl.³ ............................................. A24B 1/30
[52] U.S. Cl. .......................................... 604/52; 604/5; 604/190; 604/252; 604/406
[58] Field of Search ........... 128/214 R, 214 B, 214 C, 128/215, 221, 214.2; 210/445, 446, 499; 29/163.5 F; 604/4–6, 190, 252, 406, 52

[56] References Cited

U.S. PATENT DOCUMENTS

| | | | |
|---|---|---|---|
| 2,857,913 | 10/1958 | Miskel | 128/221 |
| 3,238,056 | 3/1966 | Pall et al. | 210/75 X |
| 3,344,785 | 10/1967 | Hamilton | 128/214 B |
| 3,722,697 | 3/1973 | Burke et al. | 128/214 C X |
| 3,782,083 | 1/1974 | Rosenberg | 210/445 X |
| 4,113,627 | 9/1978 | Leason | 210/446 |
| 4,170,056 | 10/1979 | Meyst et al. | 128/214 B |
| 4,200,096 | 4/1980 | Charvin | 128/214.4 |

OTHER PUBLICATIONS

Milipore Data Sheet SW-13-(Swinnex-13), Sep. 1965.

*Primary Examiner*—V. Millin
*Attorney, Agent, or Firm*—Cox & Smith Incorporated

[57] ABSTRACT

A microfilter and method for infusion of blood and blood components into premature or neonatal infants designed to be utilized as an interruption filter between the syringe carrying the blood to be transfused and the needle injected into the vein of the patient or stopcock connections to the vasculature of the patient. The filter of this invention includes a filter body adapted to engage a syringe nipple and a needle hub, or standard luer taper fitting. The square body of this filter encases a stainless steel filter screen passing particles of less than 18 microns in diameter and restricting or trapping particles of larger diameter. The filter functions by a sieving or direct interruption of passage of larger microaggregates. The filter is specifically designed for utilization one time only. The method includes transfusing 5 to 20 cc of blood while screening out particles of less than 18 microns.

7 Claims, 5 Drawing Figures

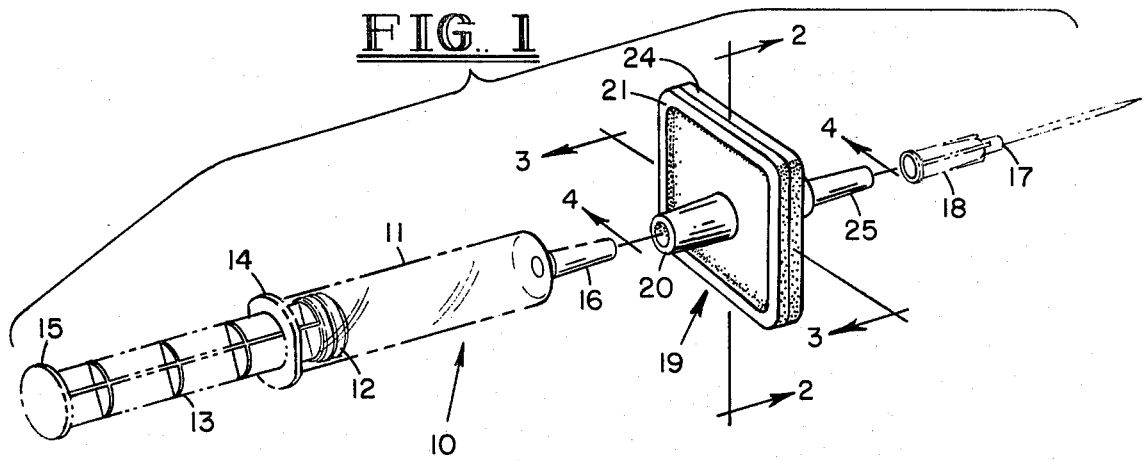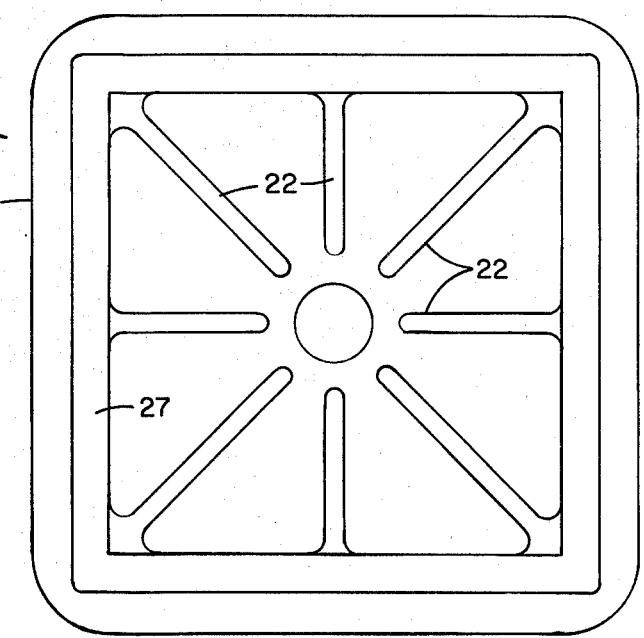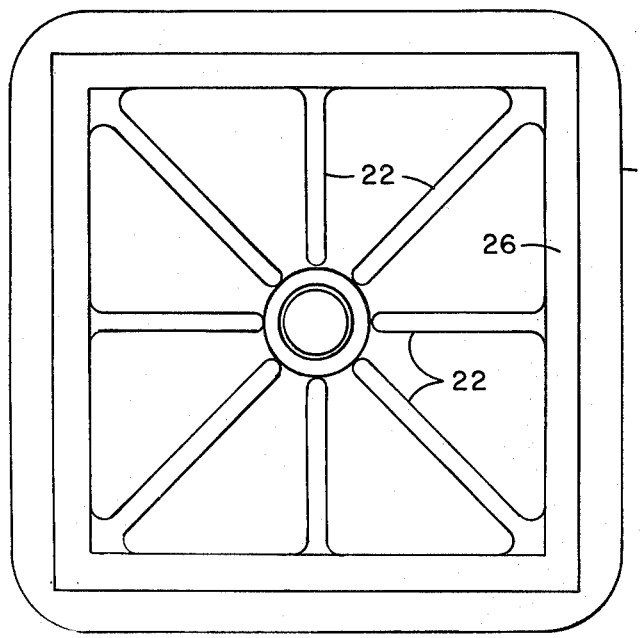

METHOD AND APPARATUS FOR MICROFILTRATION OF BLOOD

This is a continuation-in-part of application Ser. No. 10,064 filed Feb. 7, 1979, now abandoned and a continuation-in-part of application Ser. No. 362,427 filed Mar. 23, 1982, now abandoned.

BACKGROUND OF THE INVENTION

This invention pertains to a disposable filter and method for removing microaggregates from blood in limited transfusion of infants. Transfusion of premature infants and very young children present special problems in the removal of microaggregates in the blood and blood components that have been stored. The extremely small vein and capillary size of premature and neonatal infants creates hazards to damage by introduction of microembulisms or microaggregates into the circulatory system. Limited transfusions of 5 to 20 cc of blood create a desirability for a small, disposable filter which may be utilized in conjunction with an infusion needle or infusion set with stopcock and syringe.

The need for filtration of blood has been known for many, many years. In situations where a typical 18 gauge needle was utilized for getting blood into patients, such needles might become plugged with clots when the blood coming from blood banks was not treated in any manner. This problem led to the development of the 170 micron clot screen, which despite advances in handling of blood by blood banks, is still used today in some instances and is often included as part of a blood administration set.

In addition to this problem from the past, advancing medical technology has made manifest the need for finer filtration so as to protect the capillary bed of the pulmonary vasculature, thereby avoiding the possibility of the Adult Respiratory Distress Syndrome, Shock Lung or other Functional Pulmonary Abnormalities. Changes in blood are manifested almost immediately upon withdrawal from the body and are enhanced in every contact made with a foreign surface which will tend to create microaggregates. Even the type of anticoagulant used in the container for storage may influence the rate of microaggregate formation. As set forth above, microaggregates begin to form almost immediately and by the third day after removal from a human body, there are marked increases in the formation of microaggregates, and within one week the aggregation process is generally complete. Microaggregates are typically composed of platelets, nonviable leukocytes, fibrin strands (fibrinoproteins), denatured proteins and portions of cellular membranes. Microaggregates can be found in all types of blood, blood components and fractionates, i.e. whole blood, packed cells, fresh frozen plasma, cryoprecipitates and AHF concentrates. Applicant's filter will permit infusion of viable blood components such as erythrocytes, leukocytes, platelets, Factor VIII and Factor IX for treatment of hemophiliacs and other blood disorders. The volume of the microaggregates increase daily as the blood is stored.

The size and number of microaggregates is estimated to be $7 \times 10^7$ particles that are 10 microns or larger in one unit of seven-day old blood. Slightly more than one-half of the microaggregates are smaller than 20 microns in diameter. With each unit of blood, 10 to 15 million microaggregates in the range of 20 to 40 microns in diameter can be carried into the capillary bed of the pulmonary vasculature. It has also been learned that the terminal precapillary arterioles are estimated to number $2.70 \times 10^8$ and are 20 microns or less in diameter. From the above information, the importance of microaggregate filtration to remove debris in the form of microaggregates from blood and blood products has become clear.

In dealing with pediatric age group patients, the problems of blood filtration become even more critical since the pulmonary vasculature and capillary network of pediatric patients is smaller in size than in adults. The usage of microaggregate blood filters is a common practice in adult patients. However, the only filters presently available on the market are for the adult population. An example of this is shown in U.S. Pat. No. 3,701,433 issued to S. Krakaur et al. Application of adult blood filters to the administration of blood to children and neonates can cause several problems. First, the cost of an adult blood filter is relatively high, particularly when considering the frequent need for small volume infusions of filtered blood in the neonate age group. Secondly, large priming volumes are associated with adult blood filters which may exceed, by as much as 10 to 20 percent of the neonate total blood volumn. By way of example, as much as 70 ml. of blood can be wasted in priming certain adult blood filters. Thirdly, adult blood filters must be used "in-line" associated with a standard blood administration set, whereas, for small volume infusion of neonates and children, blood and blood components are generally administered by syringe. A syringe is used in order to achieve a degree of accuracy which is needed when dealing with the critical balances demanded by the neonate in particular. The above reasons, and perhaps others, effectively exclude filtration of blood, blood components and blood fractionates in the neonate group. There has long existed in the art a need for a microaggregate-type filter for pediatric patients and a method which will provide filtration of blood, blood components and other blood products to remove undesired microaggregates, while still allowing the viable components to be infused in the patient. At the same time the blood, blood components and other blood products must be treated in a gentle manner so as not to damage them.

With the discovery of the existence of microaggregates in blood stored prior to use, numerous approaches to filtration were developed. Massive transfusion involving the utilization of tens or dozens of units of blood create special problems in filtration, and solutions have been developed. The limited or special problems occur in small transfusions of premature babies and small infants. Generally, a small, compact, disposable filter is desirable in these types of transfusions.

Among the numerous types of blood filters for the filtration of microemboli which have been developed are:

The Intercept filter (the gross clot screen filter) employs an initial screen filter of approximately 170 microns. The depth filter is of woven Dacron and a final screen filter with a pore size of 20 microns.

One of the more popular and widely used filters is the Pall filter which was primarily developed for utilization in cardiopulmonary bypass in open heart surgery. This filter has a relatively long life, high capacity, and employs a clot screen and a folted, woven polyester screen with resulting 40-micron passageways.

The Biotest microfilter employs nylon screen mesh decreasing in aperture size from 200 microns down to a final state of 10 microns.

Depth filters generally employ a mass of fibrous elements through which the blood passes filtering by absorption.

The Bentley filter utilizes a type of polyurethane foam of graduated size.

The Fenwal blood filter utilizes a combination of polyester foam and more restricted portion is constructed of packed nylon fibers.

The Swank filter is an improved or modification of the old glass wool filter and utilizes Dacron wool as the filter medium.

Prior art filters frequently require from 15 to 80 cc to prime the filter. The device of this invention requires essentially no priming in that the volumetric capacity of the filter is less than 1 cc. The design of this invention results in substantial savings in blood and blood components in transfusions of infants and pediatric patients.

An object of this invention is to provide a new and useful method and apparatus for microfiltration of blood in infants which overcomes the problems associated with the prior art. Applicant's invention provides an inexpensive and effective apparatus and method for transfusion of infants. At the same time, it eliminates any of the problems associated with the prior art, which, so far as known, did not provide a solution to the problem. Other objects of the invention will become apparent from the remainder of the specification.

SUMMARY OF THE INVENTION

The apparatus and method of this invention uses a square body having an exterior dimension of approximately 1" on each side. Stainless steel, wire cloth, preferably of a Dutch twill weave, having structure and dimensions restricting the passage of particles in excess of 18 microns in size, is utilized in the construction of the screen. Stainless steel has been found more compatible with blood and has a lower Z-factor (Zeta Potential) than other materials. The filter body is constructed of plastic in two sections by injection molding. The two sections fit together over a $\frac{7}{8}$" square stainless steel wire cloth and are secured together by an ultrasonic weld. A square horn fits over the stainless steel plastic sandwich-like structure and welds the two halves and the stainless steel filter media into an integral structure. The filter requires less than 1 cc volumetric capacity for priming and preferably 0.07–0.08 cc. The filter is constructed in such a configuration as to receive a syringe-like injector at one end and fits into a conventional needle hub at the opposite end. In treatment of premature babies and very small infants having need for blood and/or blood components, transfusions in the range of 5 to 15 cc are usually performed. These small transfusions lend themselves to the utilization of these small, disposable, screen-type microfilters for removing microaggregates from the blood by a direct screening or sieving action. Although large screens and large filters have heretofore been utilized, to the best of the knowledge of your applicant, this is the first development of a small, disposable microfilter and method particularly suited for filtering blood and blood components in the process of transfusion wherein these fluids are injected from a relatively small syringe into a pediatric patient. Substantial quantities of blood and blood components are conserved by use of this invention.

BRIEF DESCRIPTION OF THE DRAWINGS

For an illustration of the construction and configuration of the device of this invention and the detailed description of the preferred embodiment, reference is made to the attached several drawings. Identical reference characters will be utilized to refer to identical or equivalent components throughout the various drawings and the detailed description which later follows.

FIG. 1 is a perspective view illustrating the combination of a syringe, the filter of this invention, and a needle.

FIG. 2 is a sectional view substantially along the line 2—2 of FIG. 1 illustrating the interior surface of the needle section of the filter body.

FIG. 3 is a sectional view substantially along line 3—3 of FIG. 1 illustrating the interior surface of the syringe end of the filter body.

BRIEF DESCRIPTION OF THE PREFERRED EMBODIMENT

Figure 4:
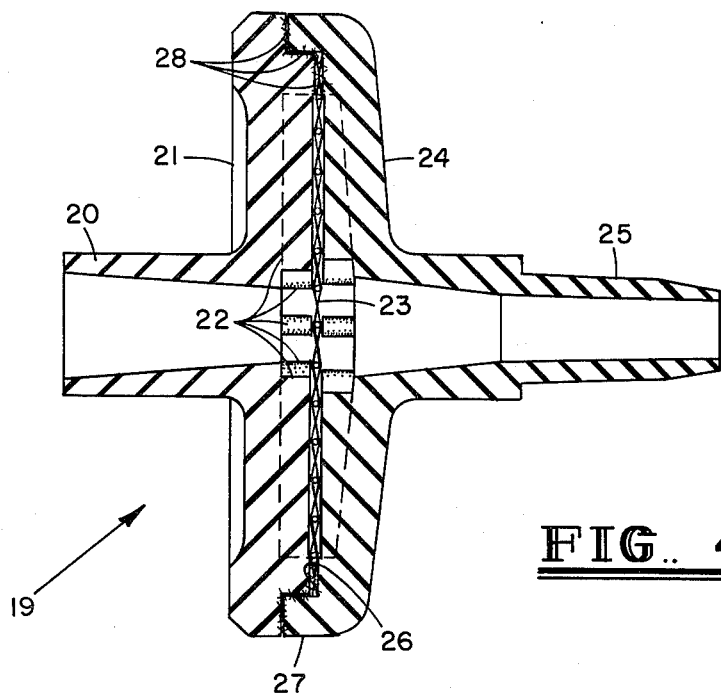
FIG. 4 is a sectional view of the filter body taken substantially on line 4—4 of FIG. 1 looking in the direction of the arrows illustrating the cross-section configuration of the composite filter structure.

It is self-evident that blood microfilters are a highly developed art; however, the particular filter of this invention comprises a small, compact, disposable, screen-type microfilter, and method, particularly adapted for transfusion of premature or neonatal infants requiring transfusions of in the order of 5 to 15 cc of blood. The apparatus and method of the preferred embodiment is designed for utilization in conjunction with various components available on the commercial market and widely used currently in the medical profession. The combined device is illustrated in FIG. 1. The syringe 10 is one of a variety of readily available syringes and needles utilized in drawing blood samples or for injections. The cylinder 11 of the syringe should preferably have a capacity from 1 to 20 cc. The piston 12 normally is of plastic or rubber-like material sealing against the inner surface of cylinder 11. Piston 12 is mounted on the end of plunger 13 which is utilized to withdraw or drive piston 12 in cylinder 11. Cylinder 11 is normally constructed with a cylinder lip 14 which facilitates grasping by the fingers in use. Plunger drive 15 is usually a round, flared structure constructed as a part of the plunger 13 at the end of the plunger 13 opposite piston 12. The needle 17 to be utilized in the transfusion procedures visualized in utilization with this device is a conventional, disposable infusion needle. Because of the small vein size of premature and neonatal infant patients, a needle size of 20 or 21 is preferable under most circumstances. Needle 17 is equipped with a needle hub 18. This needle hub 18 is the conventional, widely used, plastic-type structure generally referred to as the standard leur tapered fitting.

The gist of the invention resides in the filter 19 structure variously illustrated in FIGS. 2 through 5 and the method of use. FIG. 4, in a sectional view of the filter body, illustrates the overall arrangement of the filter structure. This device has a syringe adapter 20 at one end which may receive syringe nipple 16 in a tapered grasping contact-like engagement. The opposite end of the filter is generally referred to as the needle adapter end 24 which terminates in a needle shaft 25 having a configuration virtually identical to syringe nipple 16 to effectively engage the needle hub 18. The body syringe end 21 is constructed of plastic by injection molding and may utilize Rohm and Hass Plexiglass No. V-052. The interior configuration of this body syringe end 21 is substantially as illustrated in FIG. 3. The interior configurations of body syringe end 21 and the body needle end 24 each include screen support ribs 22 of the configuration as illustrated in FIGS. 2, 3 and 4 so dimensioned as to provide a gap of approximately 1/100″ between the screen support ribs 22 when the body syringe end 21 and the body needle end 24 are mated together in a composite structure. The purpose of this gap is to provide space for stainless steel filter screen 23. This element is constructed preferably from a Dutch twill weave stainless steel cloth having apertures of such a size and bubble-point tested as to retain particles in excess of 18 microns in diameter. In the construction and assembly of this filter 19 as previously stated, the components are preferably produced by injection molding. The relative dimensions and configurations are as illustrated in FIGS. 2, 3 and 4. Body needle end 24 is constructed with a flat smooth square in its interior dimensions as illustrated in FIG. 2. A piece of ⅜″ by ⅜″ square stainless steel cloth nestles in or fits on this square base. This section is designated as filter seat 26 in FIG. 2. The opposite end of this structure fits over and encloses the filter seat 26 with the structure constructed interior of body syringe end 21. This cup-like structure is designated as filter cap 27 as illustrated in FIG. 4.

Figure 5:
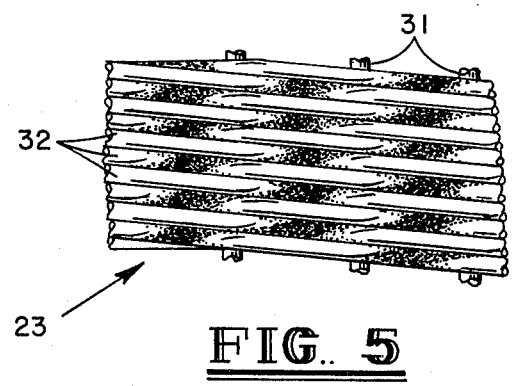
FIG. 5 is a fragmented view of a section of the preferred, Dutch twill weave, stainless steel cloth illustrating the warp and woof of the material.

In the final assembly, the body syringe end 21, filter 19, and body needle end 24 are placed in engagement and the composite device placed on a support die after which a square horn of a sonic welding machine is brought into contact with the opposite end of the device. Under pressure and supersonic agitation, the edges of the stainless steel filter 19 is embedded in the plastic components and each of the plastic components are sonicly welded to each other. This creates a hermetic and closed seal around the periphery of the composite structure. The sonic weld 28 is generally present in the area designated as 28 in FIG. 4. The stainless steel cloth of filter screen 23 of this device is preferably constructed from low carbon stainless steel. A satisfactory product is "mini-mesh" filter cloth DTW 18 165-1400 produced by Tylinter of West Germany, having an aperture size of in the order of 18 microns. The stainless steel cloth preferably is of a Dutch twill weave having an outer appearance as suggested in FIG. 5. This type of weave is generally illustrated in FIG. 5 and has a warp 31 along its length of the stringer fibers and has a woof 32 which are the cross or filler threads. The filter is a two-way or bi-directional filter in that it will filter blood being drawn into a syringe and blood being ejected therefrom.

OPERATION OF THE DEVICE

In utilization of the device of this invention, existing surgical procedures are utilized for placing the needle 17 in the vein of a premature or neonatal patient. These techniques on occasions can be quite complicated and this invention is not intended to be directed to the surgical procedures employed. With the infusion needle 17 in place, the cylinder 11 of syringe 10 is filled with the desired predetermined quantity of donor blood which may be in the order of 5 to 20 cc depending on the size and need of the patient. Filter 19 engages the syringe nipple 16 and a depressing of plunger drive 15 fills the interior sterile void or volumetric capacity of filter 19 to prime the filter. An engaging of needle hub 18 by body needle shaft 25 interconnects the components for transfusion. A depressing of plunger drive 15 will prime the filter and inject the desired number of cc of blood into the vein of the patient. The priming of the filter requires less than 1 cc to fill the volumetric capacity of the filter and preferrably requires 0.07-0.08 cc. Microaggregates having a particle size greater than 18 microns are not injected past the filter media and into the vein. The structure of this device is designed to be delivered for use in a sterile condition. Any approved method of sterilization is acceptable; however, it is visualized that the filters of this device will be packaged in blister packs with a "Tyvek" lid designed for gas sterilization. Although in this configuration, the ETO method of sterilization is visualized, it is possible to employ ultraviolet radiation or any other acceptable method of sterilization. In the utilization of the filters 19 of this device, it is visualized that sterile packets will be opened and the filter 19 removed from the packet by insertion of the sterile syringe 10 to avoid touch contamination. After utilization, it is visualized that ordinarily the needle 17, filter 19, and syringe 10 will be disposed of. The device of this invention lends itself to the disposable techniques generally used in hospitals at the present state of the art. Although autoclaving syringes of certain structures might be feasible, the filter is designed for one time use and a disposing of with no subsequent use. The nature of the structure and the particular configuration visualizes a satisfactory filtration of microaggregates on a one-shot, one transfusion procedure in small quantities of approximately 5 to 20 cc. Since the filter is a two-way filter, it may be used to filter blood being drawn into the syringe. In such cases, it would be removed or replaced before injecting the blood into the patient. In mass transfusions or transfusions of adults, other type filters of larger configurations and larger capacity would be preferable. The device of this invention is specifically designed and adapted for utilization in limited transfusions of premature or neonatal patients.

Having described the construction and utilization of this invention, what is desired to be claimed are all the modifications of the structure and method not departing from the scope of equivalents of the appended claims.

I claim:

1. A microfilter for infusing blood and blood components into infants and pediatric patients comprising:
   a filter body constructed from two plastic sections;
   the first section comprising a syringe adapter end;
   the second section comprising a needle adapter end;
   a woven filter screen retained between said syringe adapter end and said needle adapter end;
   said woven filter screen comprising a stainless steel cloth;
   said stainless steel cloth comprising a Dutch twill weave having a microaperture size of in the order of 18 microns effective to retain microaggregates 18 microns or larger in size and effective to pass particles, including viable components of blood such as erythrocytes, leukocytes, platelets, Factor VIII and Factor IX, in the order of 18 microns or smaller;
   said syringe adapter end and said needle adapter end being connected to form a filter body having a body opening constructed internal of said filter body and a multiplicity of screen support ribs internal of said filter body so positioned as to contact and support said filter screen;

said filter screen being connected to and formed in the filter body in a composite integral structure by embedding the periphery of the filter screen in the two sections by sonic welding; and the volumetric capacity of the filter being less than 1 cc.

2. The invention of claim 1 wherein:
a. a multiplicity of said screen support rubs are constructed internal of said syringe adapter end;
b. a multiplicity of said screen support ribs are constructed internal of said needle adapter end;
c. the dimensioning and spacing of said assembled structure being such that the syringe end ribs and the needle end ribs are spaced a distance equivalent to the thickness of said filter screen.

3. The invention of claim 1 further comprising: 'a. a syringe attached to said syringe adapter end, and
b. a needle attached to said needle adapter end.

4. The invention of claim 1 further comprising:
a. a syringe attached to said syringe adapter end, and
b. a leur tapered fitting attached to said needle adapter end.

5. The invention of claim 1, wherein:
the volumetric capacity is 0.07–0.08 cc.

6. A method of infusing blood and blood components in infants and neonates comprising the steps of:

removing microaggregates having a particle size greater than in the order of 18 microns from a predetermined quantity of blood and blood components while passing particle sizes including viable components of blood such as erythrocytes, leukocytes, platelets, Factor VIII and Factor IX, in the order of 18 microns or smaller;

injecting the blood and blood components including viable components of blood such as erythrocytes, leukocytes, platelets, Factor VIII and Factor IX, having a particle size in the order of 18 microns or smaller into the infant or neonate;

the step of removing including passing the blood through a filter having a stainless steel screen with a Dutch twill weave;

the step of passing blood and blood components through the filter includes priming the filter with in the order of 1 cc of blood and blood components; and the step of injecting includes injecting in the order of 5 to 20 cc of blood and blood components into the infant or neonate.

7. The method of claim 6 wherein:
the step of passing the blood through the filter includes priming the filter with 0.07–0.08 cc of blood.

* * * * *